United States Patent [19]
Frische et al.

[11] Patent Number: 5,427,790
[45] Date of Patent: Jun. 27, 1995

[54] PROCESS FOR PRODUCING A TRIGLYCERIDE MIX FREE FROM COMPONENTS HAMPERING FURTHER PROCESSING

[75] Inventors: Rainer Frische, Frankfurt; Judith Schneider, Hofheim; Erika Jager, Hamburg; Jurgen Volkheimer, Wiesbaden; Michaela Kramer, Allendorf., all of Germany

[73] Assignee: Dr. Frische GmbH, Germany

[21] Appl. No.: 980,784

[22] PCT Filed: Jun. 11, 1992

[86] PCT No.: PCT/EP92/01303
§ 371 Date: Jun. 7, 1993
§ 102(e) Date: Jun. 7, 1993

[87] PCT Pub. No.: WO92/22626
PCT Pub. Date: Dec. 23, 1992

[30] Foreign Application Priority Data

Jun. 12, 1991 [DE] Germany .................. 41 19 269.9
Jul. 24, 1991 [DE] Germany .................. 41 24 504.0

[51] Int. Cl.⁶ .............................................. C11B 7/00
[52] U.S. Cl. .................................. 424/195.1; 514/557
[58] Field of Search ...................... 424/195.1; 514/557

[56] References Cited

U.S. PATENT DOCUMENTS 4,297,292 10/1981 Logan et al. .................. 260/428

FOREIGN PATENT DOCUMENTS 0326198 8/1989 European Pat. Off. .
0367877 5/1990 European Pat. Off. .
750045 6/1956 United Kingdom .
848689 9/1960 United Kingdom .

OTHER PUBLICATIONS

U. Erasmas "Fats and Oils".
Hoffman, The Chem. and Technology of Edible Oils and Fats and Their High Fat Prodr. Head Press. London, 1990 pp. 370–371, 257–259.
Data Base WPIL, Week 9120, (Derwent Publications, Ltd. London).

Primary Examiner—Ronald W. Griffin
Attorney, Agent, or Firm—Quarles & Brady

[57] ABSTRACT

A process for producing a triglyceride mix free from components hampering further processing from a vegetable oil as a starting material, which is cooled and then separated into a predominantly solid and a predominantly liquid phase. The vegetable oil used as starting material is one in which a predetermined reactive fatty acid predominates in the fatty acid pattern with a content of at least about 80%. The cooling temperature of the cooling step is so adjusted that the particularly hard to solidify or readily soluble triglycerides in the starting material remain at least substantially liquid or in solution. In one embodiment, the solid phase obtained after the first separation step is then dissolved and cooled in a second cooling step to a temperature different from an initial temperature step at which the easier to solidify or less soluble triglycerides bearing less reactive groups separate out.

22 Claims, 6 Drawing Sheets

FIG. 2    SEPARATION SCHEME S1 FOR EXAMPLE 2

PROCESS FOR PRODUCING A TRIGLYCERIDE MIX FREE FROM COMPONENTS HAMPERING FURTHER PROCESSING

BACKGROUND OF THE INVENTION

1. Field of the Invention

This invention relates to a process for producing a triglyceride mix free from components hampering further processing or a triglyceride of single fatty acids which is at least technically pure, from a vegetable oil and/or a derivative containing the unaltered carbon framework of a vegetable oil as starting material, which is cooled as such or in solution and then separated into a predominantly solid and a predominantly liquid phase, wherein the cooling and separation of one of the phases or both phases are repeated if desired.

In the further processing of triglyceride mixes, especially in double bond derivatives formed from the oleic acid of such mixes, it is particularly important that the mix to be processed does not contain any components which undergo reactions concurrent with the reaction of the double bond of the oleic acid component. On the other hand it is not necessary to isolate the oleic acid component completely for this purpose, which would lead to unacceptably high costs.

2. Description of the Prior Art

The majority of vegetable oils, especially the agriculturally produced vegetable oils, contain as fatty acids those with chain lengths of C16 and C18, the commonest fatty acids being palmitic acid (C16), stearic acid (C18), oleic acid (C18:1), linoleic acid (C18:2) and linolenic acid (C18:3). The numbers following the colons give the number of double bonds in the fatty acid chain.

Although the majority of common fats and oils consist mainly of triglycerides of these 5 fatty acids, they exhibit in part substantial differences in chemical and physical properties. These differences arise above all in that even with only moderately different fatty acid patterns, serious differences exist in the distribution of the individual triglycerides in the oils and fats involved.

With an oil or fat with a content of 50% of one predominant fatty acid in the fatty acid pattern, there are, in accordance with the combination rules, over 150 chemically different triglycerides present in appreciable proportions, if all the above-mentioned 5 fatty acids occur in appreciable proportions in the fatty acid pattern. The "main component" is merely the triglyceride carrying the predominant fatty acid. It is however represented by only 12.5% of the total amount of triglyceride. As against this, an oil or a fat in which one fatty acid is represented by approximately 80% in the fatty acid pattern, consists practically only of those triglycerides in which the predominant fatty acid occurs at least twice. Overall such an oil consists much more than 90% of merely nine different triglycerides, when all the above-mentioned five fatty acids are present in appreciable proportions in the fatty acid pattern. Over 50% of such a fat or oil is formed from the triglyceride carrying solely the predominant fatty acid.

From the above it is clear that—if possible at all—separation of chemically uniformly constituted triglycerides is more possible with such oils and fats as those in which a single fatty acid predominates strongly.

However, even in this case the art has previously taught that the differences in physical properties of the triglycerides in question are so small that separation of the triglycerides by simple physical methods of separation would not be possible.

The production of chemically pure oleic acid, linoleic acid and linolenic acid, as well as the production of chemically pure mono, di and triglycerides of these fatty acids has been effected to date by use of extremely expensive physical and chemical methods, such as high pressure liquid chromatography (HPLC) and the chemical synthesis of the mono, di and triglycerides from the corresponding fatty acids previously rendered pure. Accordingly it is true that highly enriched triglycerides of vegetable oils or their derivatives, containing only one fatty acid type can be produced but only at very substantial cost. These lie in order of magnitude of about 10,000 DM per kg for a trioleate of high purity. With the production of the pure fatty acids practiced to date, as also the pure mono, di and triglycerides, the expense of separation and synthesis so exceeds the raw material costs that the latter are practically insignificant. Accordingly, although inexpensive raw materials with high contents of the relevant fatty acids are available and although the above-mentioned fatty acids are very suitable on account of their chemical structure as chemical starting materials (e.g. for ozonolysis), chemically pure reactive fatty acids play no part in the industrial field of technology on account of the lack so far of the possibility of producing them in chemically pure form.

In what follows, the invention will be described using the example of such triglyceride mixes as contain oleic acid as an essential component. The invention can however be similarly employed with other triglyceride mixes.

Oleic acid represents one of the most important raw materials of oleo-chemistry as a whole. It occurs in vegetable and animal oils and fats, accompanied by a plurality of other saturated and unsaturated fatty acids of various chain lengths, in part multiple unsaturated, above all as triglycerides. As a rule, especially with the fats and oils of technological interest, the fatty acids with chain lengths between $C_{12}$ and $C_{22}$ predominate, the $C_{18}$ fatty acids in turn being especially strongly represented.

Although a number of methods for converting oleic acid into reaction products are used industrially—one of the most important conversions of oleic acid is ozonolysis, in which the oleic acid is split by oxidation into azelaic acid and pelargonic acid—the raw material used for oleo-chemistry is not pure oleic acid by merely enriched oleic acid. As a rule, the concentration of oleic acid in the raw material amounts to 72 to 75%. Such enriched fractions are obtained from inexpensive tallow. It has been found that a higher enrichment than 72 to 75% oleic acid content in the reaction product cannot be implemented without renouncing the price advantage of tallow as raw material. The enrichment mechanism used for this also disproportionally enriches the many unsaturated fatty acids which may be present.

The object of the invention is therefore firstly to provide a process in which raw material is produced for the further processing of triglyceride mixes, especially for the derivative formation from the oleic acid components of such mixes, which contain the components of interest more strongly enriched and which moreover contain hardly any components which interfere with the further processing, especially no or hardly any multiple unsaturated fatty acids. Furthermore a process is to be provided capable of producing economically at least technically pure and preferable highly pure triglycerides, containing only a single fatty acid type, such as for example trioleate, from vegetable oils or their derivatives as starting materials.

Oil seeds have recently been grown in whose oils oleic acid in natively present in amounts of above about 80% ("high oleic oil"). The performance of reactions with the oleic acid is thus effectively facilitated. The stated limit of 80% is not to be regarded as rigid; thus sunflower oil with an oleic acid content of a little above 78% is likewise to be called a high oleic oil.

SUMMARY OF THE INVENTION

It has now surprisingly also been found that it is possible—starting from such high oleic oils—to divide the starting oil into a fraction in which only saturated fatty acids and oleic acid are contained, where the content of oleic acid in this fraction is increased relative to the starting concentration, and into another fraction, in which are contained the multiple unsaturated fatty acids as well as oleic acid, where the content of oleic acid is reduced in this fraction. With this partitioning it is now possible to separate out the multiple unsaturated fatty acids already in the triglyceride stage, which are also reactive and hence interfering, before carrying out chemical reactions on the double bond of the oleic acid.

The subject matter of the invention is a process for producing a triglyceride mix free from components hampering further processing or a triglyceride of single fatty acids which is at least technically pure from a vegetable oil and/or a derivative containing the unaltered carbon framework of a vegetable oil as starting material, which is cooled as such or in solution and then separated into a predominantly solid and a predominantly liquid phase, wherein the cooling and separation of one of the phases or both phases are repeated if desired. The method is characterized in that (a) a vegetable oil is used as starting material in which a predetermined reactive fatty acid predominates in the fatty acid pattern with a content of at least about 80%, (b) the cooling temperature of a first or a single cooling step is so adjusted that the particularly hard to solidify or readily soluble triglycerides in the starting material, which as a rule contain more reactive groups, remain at least substantially liquid or in solution, (c) if desired the solid phase obtained after the first separation step is then dissolved and cooled in a second cooling step to a temperature different from the temperature in step (b), at which the easier to solidify or less soluble triglycerides bearing less reactive groups separate out at least substantially, and (d) in any event the finally obtained solid and liquid phases are separated and used, if desired after the first and/or the two cooling and separating steps have been repeated one or more times.

According to the process in accordance with the invention, instead of the usual vegetable oils or their derivatives, such vegetable oils are used as starting materials as those in which a reactive fatty acid predominates in the fatty acid pattern to at least about 80%. In the following separating process this dominance is maintained. If desired, the efficiency of the separation is appreciably increased according to the invention by an alternate separation in two sequential cooling and separating steps (a) and (b) at different temperatures—in the first separating step the solid phase is used and in the second separating step the liquid phase. Through this at least technically pure triglyceride containing only a single fatty acid type can be obtained.

Fatty acids for example containing double bonds or epoxy groups or functional groups obtainable from epoxy groups by opening the ring or combinations of groups are indicated as reactive fatty acids.

In contrast to normal multi-stage separation processes, the cooling temperature of the first cooling step is preferably selected to be lower than that of the second cooling step. This results in matching the requirement so to select the cooling temperature of the first cooling step that (as calculated) the portion of the triglyceride which is not of homogeneous composition and is more easily soluble remains in solution, while the cooling temperature of the second cooling step is so selected that the portion of the triglyceride which is not of homogeneous composition and is soluble with more difficulty precipitates out.

The liquid phase of the first separating step can also be separated out and be used like the solid phase of the second separating step without restriction.

What is significant for the separation process of the invention is not so much the solvent employed, the ratio of solvent to oil and the temperature levels maintained in the fractionating as rather, through the choice of the solvent, the mixing proportions of solvent to fat or oil and of the temperature interval to obtain good phase separation, so that a sufficiently simply separation of the phases from one another is possible and the phases currently forming on freezing contain the fractions dependent on the fatty acid pattern.

If a start is made from high oleic oil for example which has 80% oleic acid in the fatty acid pattern, this oil contains around 50% glycerine trioleate. If it is further taken that the saturated fatty acids and likewise the unsaturated fatty acids in the fatty acid pattern each occupy 10% of the fatty acid pattern (80+10+10=100), the remainder of the oil consists of 25% of triglycerides which are more strongly saturated than the trioleate and 25% which are more unsaturated than the trioleate. It is then appropriate so to design the first fractionating step that 75% of the original oil precipitates out as solid phase and 25% of the oil remains in the liquid phase. If now an attempt were made to make this fractionation solvent-free, it would be technically practically impossible to separate a liquid phase from the solid phase which precipitates out—although it is present. In order to facilitate this separation, a solvent is used in which the vegetable oil is sufficiently soluble and from which a sufficiently rapid solid phase separation can be achieved. Suitable solvents for this are for example acetone, methyethylketone, acetic acid esters and mixtures of these solvents. The mixing proportion of oil to solvent is freely selectable in principle within wide limits.

Understandably, the separation of a crystalline solid phase from a liquid phase is especially good when the proportion of the liquid phase and thus the solvent proportion is especially high. If in fact the solid phase is filtered off, some residual liquid phase does indeed adhere to the crystalline solid phase; however, on account of the high thinning, only a little vegetable oil is contained in this, so the separating action is especially high. On the other hand, if the main quantities—in the present instance 75% of the oil used—are to be separated out as solid phase from a thinned solution of vegetable oil in solvent, this requires very low temperatures, whereby the expense of the separation is increased and handling is made more difficult. Furthermore the solubility of the different triglycerides depends strongly on the kind of solvent; it is thus possible through the choice of the solvent to alter the soluble proportion of the triglycerides at the temperature currently used for the fractionation, as is apparent from the embodiments below.

Which solvent, what fractionating temperature and what degree of thinning are finally selected depends on the triglyceride distribution calculated on the basis of the fatty acid pattern and on the possibilities in terms of apparatus.

The derivation of trioleate from high oleic oils can thus for example be effected in that initially the solid phase is separated out from a 3:1 acetone/high oleic acid mixture several times at $-27°$ C. The liquid phases then contain the enriched triglycerides containing linolenic and linoleic acids. (They cannot be separated out all at once since, at $-27°$ C. the amount of triglyceride to be separated out is not soluble well enough in the amount of solvent. If the separation is carried out at $-20°$ C. with the same thinning, the liquid phase does contain more triglyceride to be separated, which is however more concentrated in the liquid phase adhering to the crystalline slurry (solid phase), so that the isolated solid phase material has to be fractionated again to obtain a separation.) The oil precipitating out as solid phase at $-27°$ C. is then dissolved 3:1 in acetone again and fractionated several times at $-5°$ C.

The solid phases precipitating out at $-5°$ C. contain the triglycerides carrying the saturated fatty acids strongly enriched, whereas the trioleate remains in the liquid phase.

It has proved to be particularly advantageous in this separation to carry out the fractionation at about $-27°$ C. (deep freeze chest) and at about $-5°$ to $-10°$ C. alternately, so that the ratio of the triglycerides which are more soluble than trioleate to the triglycerides which are more difficult to dissolve is not shifted too far to one side with the repetition of the fractionating steps. This would of course be desirable in a conventional fractionation but apparently leads with triglycerides to a reduction in the yield of the trioleate to be obtained.

This shows that the fractionation of triglycerides is not based in simple, mathematically determinate rules of physical chemistry—as are usually applicable to fractionating operations. It is conceivable that for example the content of trioleate in the phases to be separated (in comparison with the triglycerides better soluble than trioleate and in comparison with the triglycerides less soluble than trioleate) depends on the content of non-trioleate components in the trioleate phase. This is supported by the fact that the phase of the better soluble triglycerides which can be obtained from an acetone/high oleic oil mixture (3:1) always also has a content of poorly soluble triglycerides and trioleate. This does not alter when the temperature is further reduced; rather the total amount of the soluble triglycerides then increases very strongly. The same applies correspondingly to the fraction of the poorly soluble triglycerides.

The derivation of trilinoleate or trilinolenate is possible in principle likewise by fractionating suitable oils rich in linoleic acid or linolenic acid. Oils with contents of $\geq 80\%$ of these acids in the fatty acid pattern are however not available in practice.

Normal sunflower oil and thistle oil however contain about 75% linoleic acid in the fatty acid pattern. With the process according to the invention it is possible to derive from these oils at least very strongly enriched trilinoleate in high yields—however with markedly changed separation conditions (different temperature interval and/or different solvent).

The calculation of the yield should only be related to the actual trilinoleate available in the starting oil. This is about 42% of the total amount of the starting oil with 75% linoleic acid in the fatty acid pattern.

If special chemical operations designed for the reaction of double bonds are carried out with the fraction obtained according to the process according to the invention, only the oleic acid reacts, since the other unsaturated fatty acids are absent. Naturally the saturated fatty acids do not react either. In this it is unimportant whether this reaction is carried out with the triglyceride itself or with reaction compounds, say the fatty acids and fatty acid esters derivable from the triglycerides. Among such reaction compounds there belong in particular the fatty acids, the methyl and ethyl esters of the fatty acids as well as amides, diamides of the fatty acids and aliphatic alcohols.

An advantage of the invention consists also in that, with the derivative formation from the oleic acid in the product obtained according to the invention, the separation of the reaction compounds of the oleic acid resulting from conversion of the double bond to derivatives is markedly facilitated. Thus the saturated fatty acids—as a rule this means palmitic and stearic acid—can be separated substantially more easily from such derivatives and/or reaction products of the oleic acid than from the oleic acid itself. This is shown in the example of ozonolysis, in which the final palmitic and stearic acids are separated from the oleic acid reaction products.

If the oleic acid fraction obtained in accordance with the invention is used as raw material for ozonolysis, its superiority over other comparable raw materials is especially clear:

(1) The ozone usage is determined exclusively by the oleic acid to be converted and not—as is the case at present—also by other unsaturated fatty acids, especially multiple unsaturated fatty acids. The multiple unsaturated fatty acids especially have a particularly high ozone usage, because one equivalent of ozone is used per double bond. It is noted that the ozone usage is the cost-intensive factor in the ozonolysis.

(2) Since no fatty acid reacting with the ozone is present other than the oleic acid, there are no reaction products of the ozonolysis such as usually result at present with the raw material used for ozonolysis. Thus there previously resulted from linoleic acid azelaic acid as dicarboxylic acid as with oleic acid, but also hexanoic acid and malonic acid. These two compounds make it harder to obtain the desired products of the ozonolysis, namely pelargonic acid and azelaic acid. Similarly, with linolenic acid there result propinic acid, malonic acid and azelaic acid. These unwanted side reactions increase the trouble and the costs of the ozonolysis substantially.

The oleic acid fraction obtained in accordance with the invention from high oleic oil contains other saturated fatty acids as well as oleic acid. This content of saturated fatty acids does not impinge on the ozonolysis; on the contrary, since the ozonolysis contains liquid, saturated fatty acids in any case—as a rule pelargonic acid—in order to avoid too high an ozonide concentration, the saturated fatty acids present in the oleic acid fraction obtained in accordance with the invention facilitate the reaction. The pelargonic acid as a desired reaction product of the oleic acid ozonolysis can be separated simply therefrom but the saturated fatty acids themselves assume the needful function of a solvent for the reaction.

The process according to the invention thus substantially facilitates the conversion and obtaining of reaction products from oleic acid, which result from conversion of the oleic acid at the double bond.

The process according to the invention for obtaining simply oleic acid as raw material containing unsaturated fatty acid uses high oleic oil as the starting material, i.e. native oils with a content of at least 80% oleic acid in the fatty acid pattern; they can be of varying qualities. Suitable raw materials for the process according to the invention are raw high oleic oils obtained simply by pressing oil seeds, as well as highly refined high oleic oils freed of free fatty acids, glutinous materials, coloring materials and other accompanying substances. The quality of the starting material has in practice neither a negative influence on the ability to perform the process and its efficiency, nor do the obtainable fatty acid fractions differ in their suitability for the fatty acid derivative formation processes. Only the fraction carrying the multiple unsaturated fatty acids has clearly differing qualities depending on the starting material.

Since the process according to the invention involves a physical process of separation which does not effect any chemical change of the starting oil, the fraction carrying the multiple unsaturated fatty acids can be used in practice for any use corresponding to the fatty acids composition, accordingly also for nutritional purposes.

From the point of view of cost, it can thus be advantageous to effect the obtainment of the fatty acid fraction starting from unpurified oils and then to subject the resultant fraction containing the multiple unsaturated fatty acids to a conventional process of purification. In this manner a major amount of the starting material is separable as oleic acid fraction, without expensive processes of purification having to be carried out already. The side fractions containing the impurities of the starting material, which form only a small proportion of the starting material, can then be purified through conventional purifying operations, as a rule overall more efficiently and with smaller losses than with purification of all of the starting material, accordingly with substantially reduced costs.

Accordingly, applied to the triglyceride mix containing mainly oleic acid, the process according to the invention consists in that the starting material is cooled to a temperature at which only the triglycerides containing the multiple unsaturated fatty acids remain liquid. All other triglycerides, accordingly triglycerides which contain saturated fatty acids and oleic acid are solidified at this temperature or crystallized out.

The process according to the invention involves knowledge which comes from known, empirical observations and combines this with new knowledge valid only for high oleic oils and not made accessible to the art on account on preconceptions. Thus it is known-from experience that triglycerides have a lower hardening point the higher the proportion of unsaturated fatty acids. The art has however previously missed that fact that with high oleic oils, even with static distribution of the fatty acids in the triglyceride—otherwise than is the case with conventional oils—fewer, chemically homogenous triglycerides determine the quantity of the oil.

As already mentioned above, with a fatty acid content of approximately 80%, as is always attained with high oleic oils, 50% of the vegetable oil is formed from chemically homogeneous trioleate. The remaining 50% is formed predominantly from triglycerides which contain as well as another fatty acid residue, two oleic acid residues chemically bound in the triglyceride. Triglycerides with only one or hardly any oleic acid residue are in negligible amounts in high oleic oils—otherwise than is the case with conventional oils. From this knowledge typical of high oleic oils it can be deduced that the main amount of the multiple unsaturated fatty acids in accompanied in the triglyceride by two oleic acid residues and thus should lie below the trioleate in relation to the hardening or freezing point.

The process is further facilitated in that the readiness to crystallize of the trioleate on account of its high content in comparison with conventional oils should increase strongly.

In addition the saturated fatty acids are present in high oleic oils as triglycerides in the main amounts bound with two oleic acids. These triglycerides should thus lie higher in relation to their hardening point than the corresponding triglyceride which contain multiple unsaturated fatty acids.

From general knowledge it would however be expected that, in spite of this mainly theoretical possibility of separation of the triglycerides through the readiness to crystallize and the difference in the hardening points, a clean separation would not be possible, 1. because the differences are too small, especially when it is considered that in practically all triglyceride molecules in high oleic oils, at least two oleic acid residues are chemically bound,
2. because inclusion and formation of "false" triglycerides in the crystallizing out and freezing out of the relevant phases takes place or quasi-eutectic mixtures of the triglycerides result on account of the extremely similar chemical structure. These arguments frequently form the basis for the assertion that purification of fatty acids is not possible.

Surprisingly it is possible according to the process of the invention to avoid co-precipitation or inclusion of interfering triglycerides hampering the separation, or this course of events hampering the separation does not take place.

The process according to the invention for separating solely oleic acid as triglycerides containing unsaturated fatty acids from high oleic oils can be carried out in conventional plants, but the temperature profile to be followed must be matched to the changed target composition. The process is thus so designed that there is finally obtained as the liquid phase the proportion of triglycerides which can be determined from or calculated from the fatty acid pattern of the high oleic oils, with multiple unsaturated fatty acids. A certain safety margin of 10 to 20% related to the part of the triglyceride amounts containing multiple unsaturated fatty acids to be separated out should be included in the calculation.

The process according to the invention can be carried out with the aid of suitable solvents, such as acetone or acetic acid esters, for example. The use of solvents has the result that, on account of the thinning effect, the separation of the liquid phase of the triglyceride is substantially more efficient per fractionating step, so that the number of fractionating steps can be reduced. This is important especially for batch processes. The solvent can in any case be fed into the circuit.

BRIEF DESCRIPTION OF THE DRAWINGS

The invention will be explained in more detail below in conjunction with embodiments and with reference to the drawings, in which.

DESCRIPTION OF THE PREFERRED EMBODIMENTS

The invention is disclosed in further detail by means of the following examples which are set forth for the purpose of illustrating the invention, but in no way are to be considered as limiting the invention in spirit or scope. In the examples and associated chromatograms (FIGS. 3 to 6), the following meanings apply:

O = oleate
L = linoleate
E = linolenate

Accordingly OOO = (glycerine-)trioleate
or OOL = (glycerine-)dioleate-monolinoleate.

Figure 1:
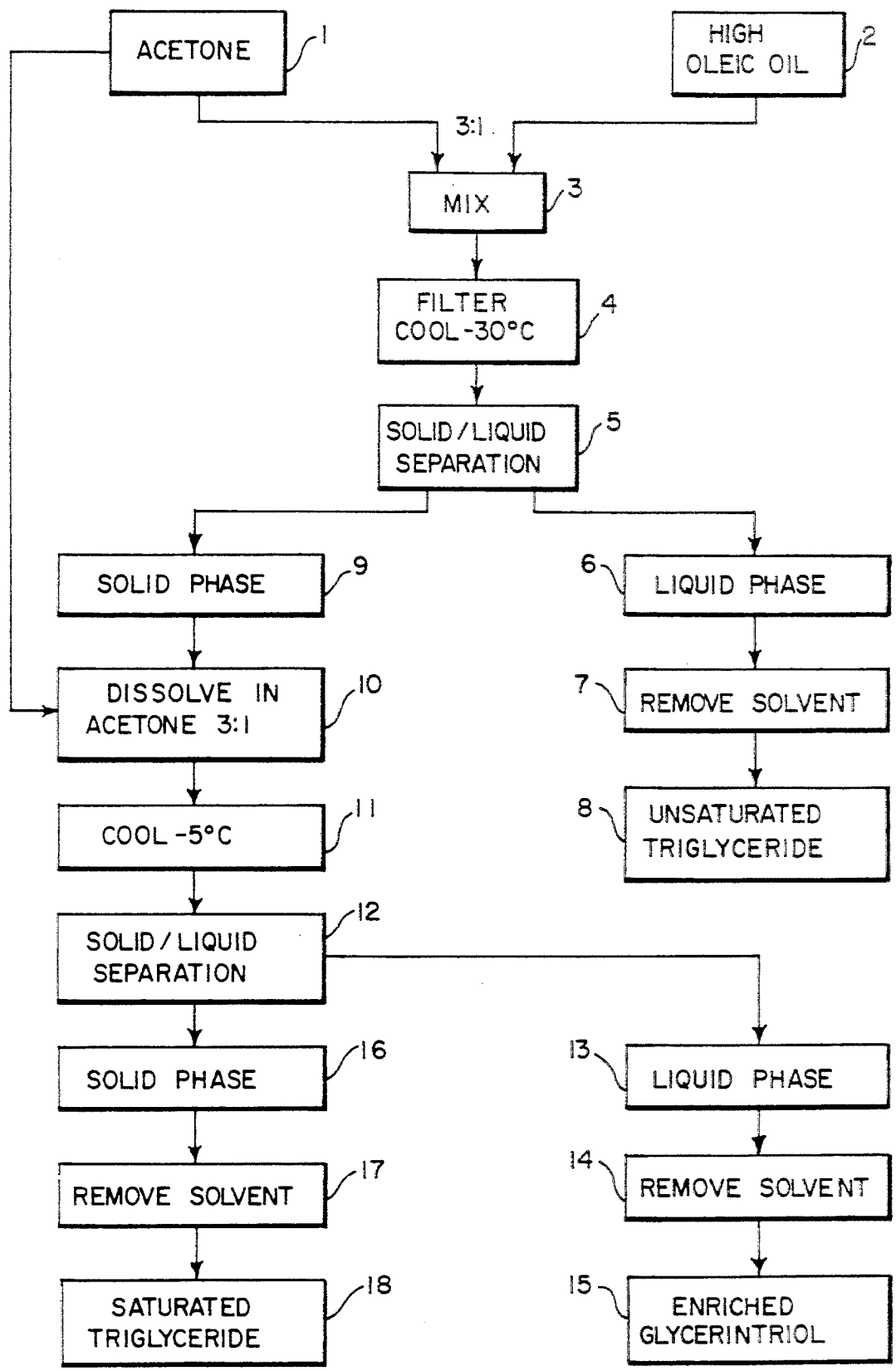
FIG. 1 is a flowchart for a fractionated glyceride separation in general form according to the invention.

The diagram according to FIG. 1 explains a fractionated triglyceride separation by the process of the invention, in which the two separation steps (b) and (c) are implemented and which leads to pure glycerine trioleate.

Acetone 1 and vegetable oil 2 (here denoted high oleic oil), in which a reactive fatty acid predominates in the fatty acid pattern with a content of at least 80%, are mixed at 3 in the ratio of for example 3:1. The mixture is then filtered if desired (with raw oils) and cooled to $-30°$ C., as indicated in the box 4. There then follows the separation symbolized by box 5 into a solid and a liquid phase.

From the liquid phase 6 the solvent is removed according to box 7 and the better soluble triglycerides are obtained, as indicated at 8, mainly not homogeneously composed, unsaturated triglycerides.

The solid phase 9 is dissolved in acetone, for example in the ratio 3:1, as shown in box 10. The solution is then cooled to $-5°$ C.; see 11. The separation into the solid and the liquid phases then follows; see box 12.

The liquid phase of the separation step 12 is shown at 13 and the solvent is removed therefrom, as shown at 14. Enriched glycerine triglyceride is obtained from this, 15.

The solvent is removed from the solid phase 16 of the separation step 12, as shown at 17 and one obtains the less easily soluble saturated triglycerides 18, mainly not homogeneously composed.

The above-described cooling and separating steps are repeated one or more times if desired.

The separation process can be applied similarly to epoxidized high oleic oils as well as to the derivatives obtainable by reductive and/or hydrolytic opening of the epoxy ring, with one hydroxyl group per epoxy group (reductive opening) or two hydroxyl groups per epoxy group (hydrolytic) or a ketone group per epoxy group (ring opening with Lewis acids).

In a similar way it is possible to isolate the triglyceride of ricinoleic acid or the triglyceride of 12-hydroxystearic acid from castor oil and from hydrated castor oil.

EXAMPLE 1

Fractionation of Euphorbia Oil with Acetone

Raw high oleic euphorbia oil (obtained by pressing seeds of *euphorbia lathyris*) is mixed with three times its amount of acetone. This results in a cloudy, slightly yellow colored, homogenous solution. The cloudiness is attributed to non-triglyceride impurities of the pressed oil. It can largely be removed by filtration of the acetone and vegetable oil solution.

The resultant filtered solution is slowly cooled (overnight) to $-28°$ C. A nearly colorless crystal slurry precipitates out, which is sucked out hard with a precooled suction filter.

The liquid phase contains the triglycerides carrying multiple unsaturated fatty acids, the solid phase essentially trioleate and triglycerides, which each contain a saturated fatty acid (palmitic acid, stearic acid) as well as oleic acid.

The fatty acid pattern of the solid phase shows from the chromatogram that the multiple unsaturated fatty acids (linoleic and linolenic acid) of the euphorbia oil are largely removed. The fatty acid pattern of the liquid phase shows that the multiple unsaturated fatty acids are concentrated therein. It is to be noted in this that the liquid phase in the fatty acid pattern comprises above all oleic acid; this is because the multiple unsaturated fatty acids must be present bound in triglyceride in each case with two oleic acid residues in the euphorbia oil.

If the separation operation is repeated—the solid residue of the vegetable oil precipitating out at $-30°$ C. is again dissolved in three times its amount of acetone and precipitated out again at $-30°$ C. and freed from solvent—the content of multiple unsaturated fatty acids in the solid fraction can fall further. Understandably there remain in the liquid phase higher amounts of oleic acid in the form of triglycerides than have to be separated out according to the computation of the proportion of triglycerides with multiple unsaturated fatty acids.

The flitrate of the low temperature crystallization process can be used for the preparation of an oil whose quality corresponds to that of a strongly unsaturated vegetable oil. In this—depending on the quality of the starting material and the kind of freezing process—solvent possibly present is removed and the conventional operations of purifying are carried out as with unsaturated vegetable oils (de-acidify, remove glutinous material, remove colorants, deodorize, etc.). The by-product thus obtained is at least as valuable as the starting material, even if it is not a high quality product, and can be employed for a variety of uses.

EXAMPLE 2

Figure 2:
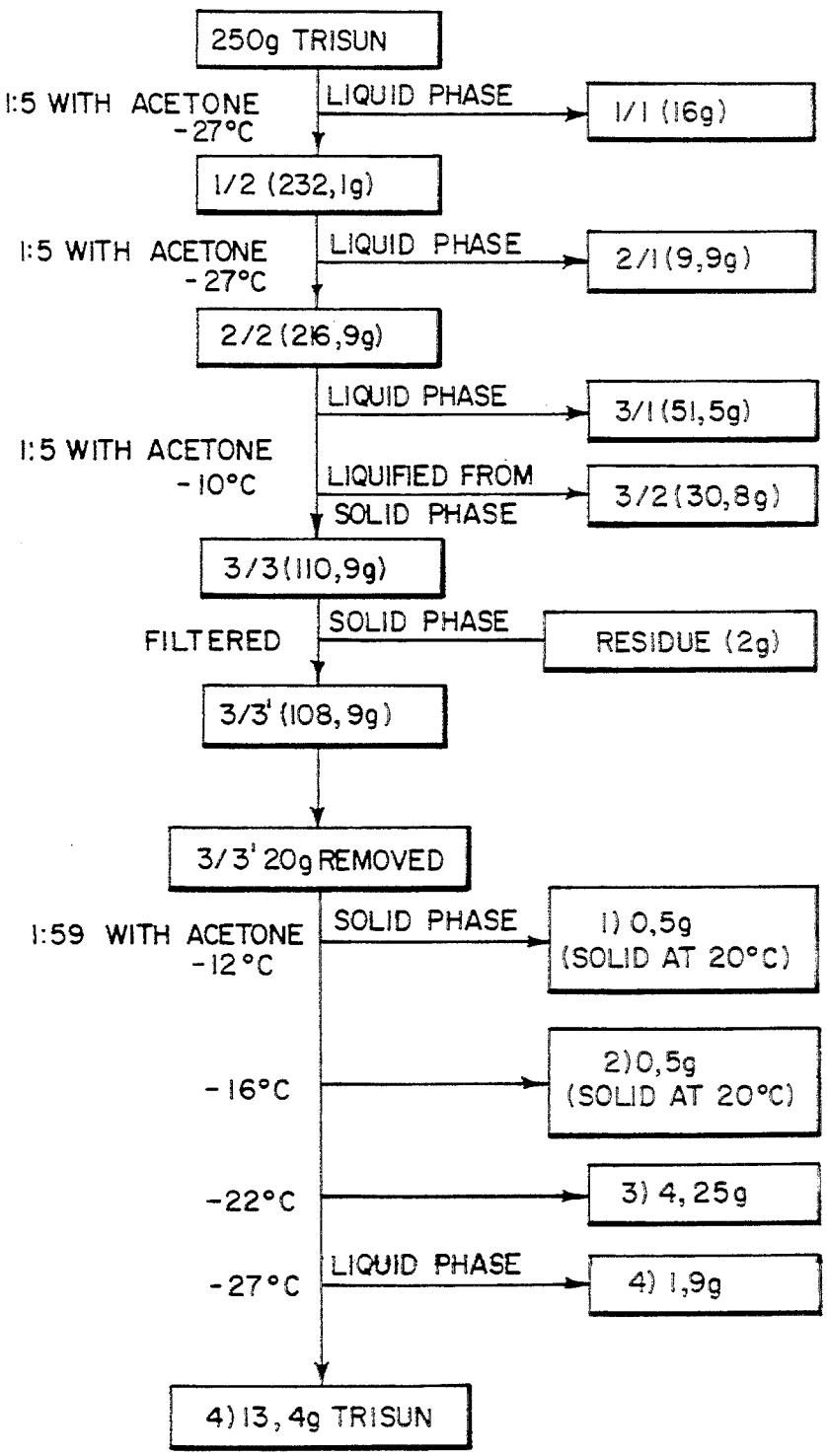
FIG. 2 is a flowchart for the fractionated glyceride separation of a high oleic sunflower oil according to the invention, as is described in example 2.

Fractionation of Sunflower Oil with Acetone: cf FIG. 2

250 g sunflower oil "TRISUN 80 RBD", batch SC 1270, which contained on analysis:

C 18:1 78.55%
C 18:2 10.70%
C 18:3 0.19% was mixed with 1250 g acetone (1:5 ratio by mass). The solution was kept overnight in the deep cooling compartment at $-27°$ C. Then the frozen solid phase 1/2 was separated from the liquid phase 1/1 through a pre-cooled fritted glass filter. The acetone was removed from the two phases by means of a rotary vaporizer.

| Yields: | 1/1 Trisun in liquid phase: | 16 g |
|---|---|---|
| | 1/2 Trisun in solid phase: | 226.5 g |

This operation was repeated again with the oil from the solid phase; i.e. it was mixed with acetone in the ratio 1:5 and kept overnight in the deep cooling compartment at −27° C. Solid and liquid phases were separated as described above and the yields determined:

| Yields: | 2/1 Trisun in liquid phase: | 9.9 g |
|---|---|---|
| | 2/2 Trisun in solid phase: | 216.9 g |

The oil from the solid phase was now again mixed with acetone in the ratio 1:5 and kept overnight in a cryostatic bath at −10° C. The resultant solid phase was now separated from the liquid phase 3/1 through a pre-cooled fritted glass filter. On further standing of the solid phase a portion of this phase liquified and was likewise removed from the remaining solid phase.

| Yields: | 3/1 Trisun in liquid phase: | 51.5 g |
|---|---|---|
| | 3/2 Trisun is solid phase (liquified): | 30.8 g |
| | 3/3 Trisun in solid phase: | 110.9 g |

Figure 3:
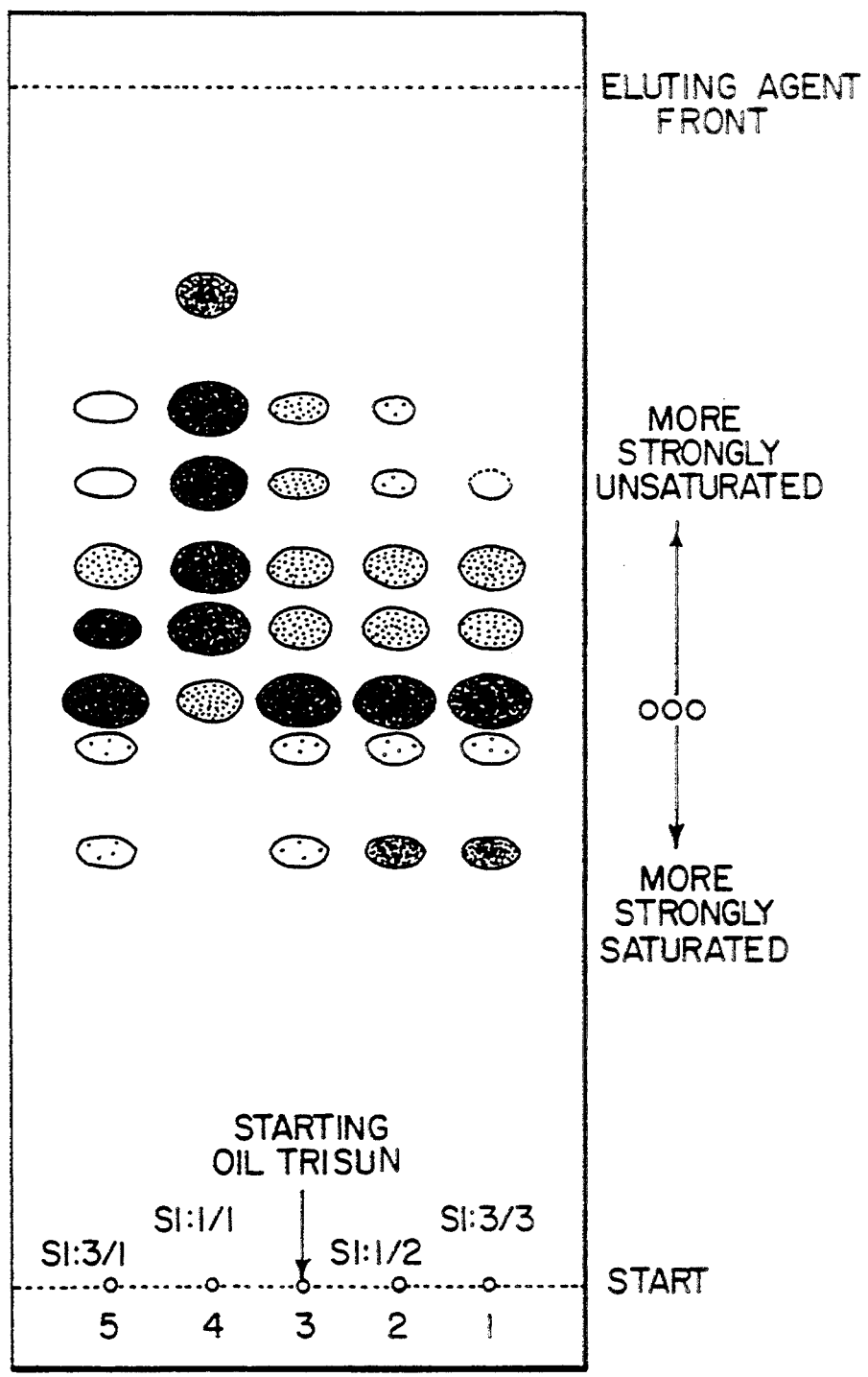
FIGS. 3 to 6 are illustrations of thin film chromatograms which show the composition of individual fractions, as are obtained in the fractionated glyceride separation according to the examples of the invention.

The chromatogram in FIG. 3 shows some of the phases in comparison with the starting oil. The liquid phase 1/1 shows a clear increase in the spot intensity for triglycerides containing multiple unsaturated fatty acids. Solid phase 3/3 shows a clear reduction of this intensity.

The following is a description of the materials and conditions employed in conjunction with FIG. 3:
Plate: HPTLC ready plate RP 18 without fluorescent indicator
  Merck: Type No. 5914
Eluting agent: acetone
Sample thinning: 20 mg/ml $CHCl_3$
Time of elution: 1 h, 20 m.
Spraying reagent: molybdenum phosphoric acid (5% in ethanol)
The analyses show the following compositions for the liquid phases:

| 1/1 Trisun in liquid phase (−27° C.): | C16:0 = 3.58% |
|---|---|
| | C18:0 = 1.68% |
| | C18:1 = 41.57% |
| | C18:2 = 51.34% |
| | C20:0 = 0.20% |
| | C22:0 = 0.32% |
| 2/1 Trisun in liquid phase (−27° C.): | C16:0 = 3.64% |
| | C18:0 = 1.70% |
| | C18:1 = 45.21% |
| | C18:2 = 48.52% |

In the next steps those triglycerides are separated out which contain the saturated fatty acids, in order to obtain at the end the purest possible trioleate.

Phase 3/3 is milky-clouded. It is filtered. A gray residue (2 g) remains on the filter.

From phase 3/3′ (filtered; clear, light yellow) 20 g are taken and mixed with 1.5 liter (1.185 kg) acetone (1:59 parts by mass). The solution was placed in the deep freeze chest.

(1) After about 2 hours at a solution temperature of −12° C. there formed a first, voluminous; flocculent, white precipitate (very little). After filtering through a pre-cooled flitted glass filter and removal of acetone with a rotary vaporizer, there remains a residue of 0.5 g, which is solid at room temperature.

(2) The liquid phase is cooled further in the deep freeze chest. At −12° C. the second precipitate is filtered off. After removal of the solvent a residue remains of about 0.5 g, which is solid at room temperature.

(3) The liquid phase is cooled further. At −22° C. the next precipitate is filtered off. After the acetone is removed with a rotary vaporizer, there remains a residue of 4.3 g, which is present as an oil at room temperature.

(4) The liquid phase is now left overnight in the deep freeze chest at −27° C. Then it is filtered through a pre-cooled fritted glass filter and the solvent removed from both phases.

| Yields: | Trisun in liquid phase: | 1.9 g |
|---|---|---|
| | Trisun in solid phase: | 13.4 g (corresponding to a 30% yield, referred to the starting amount of 250 g) |

Figure 4:
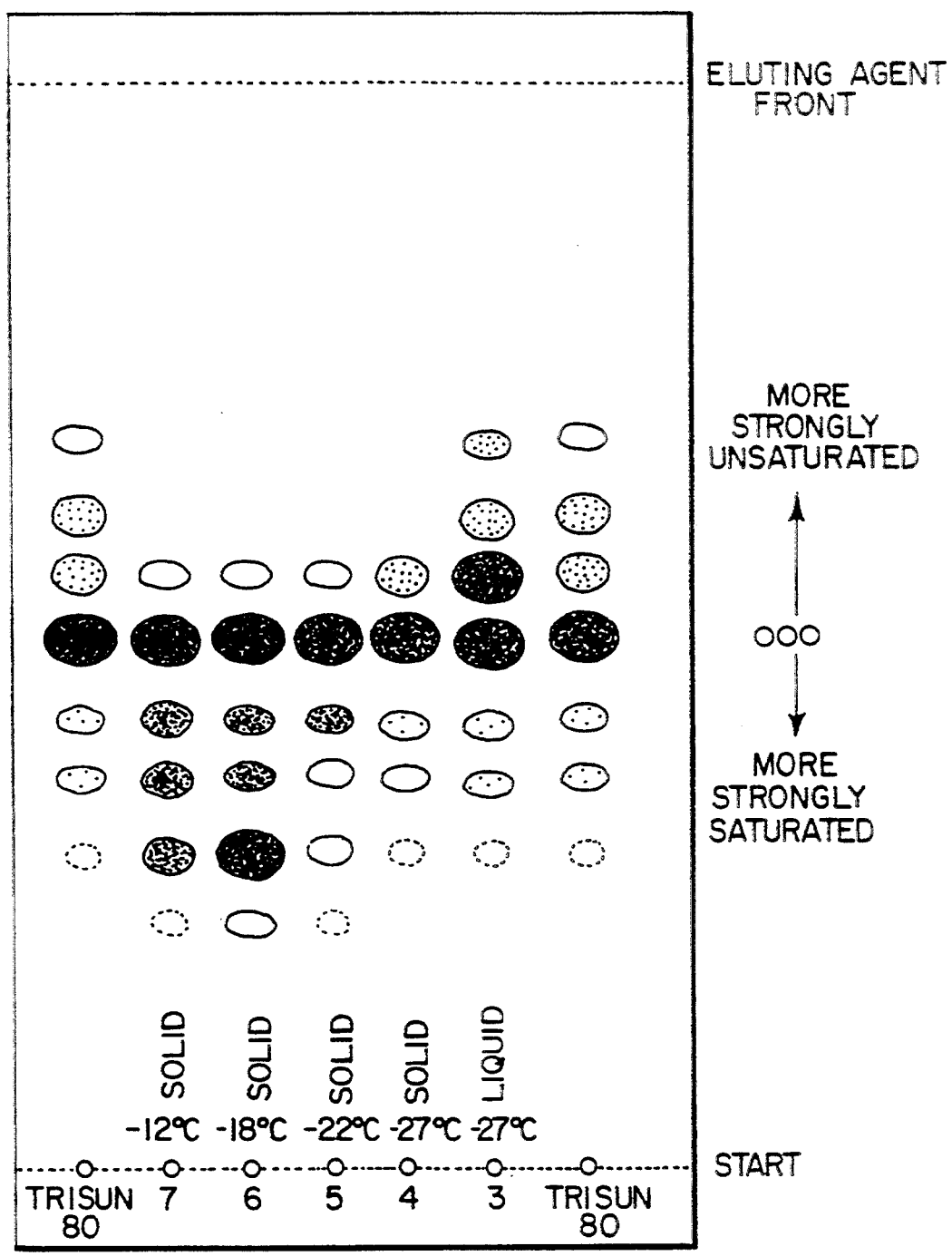
Figure 5:
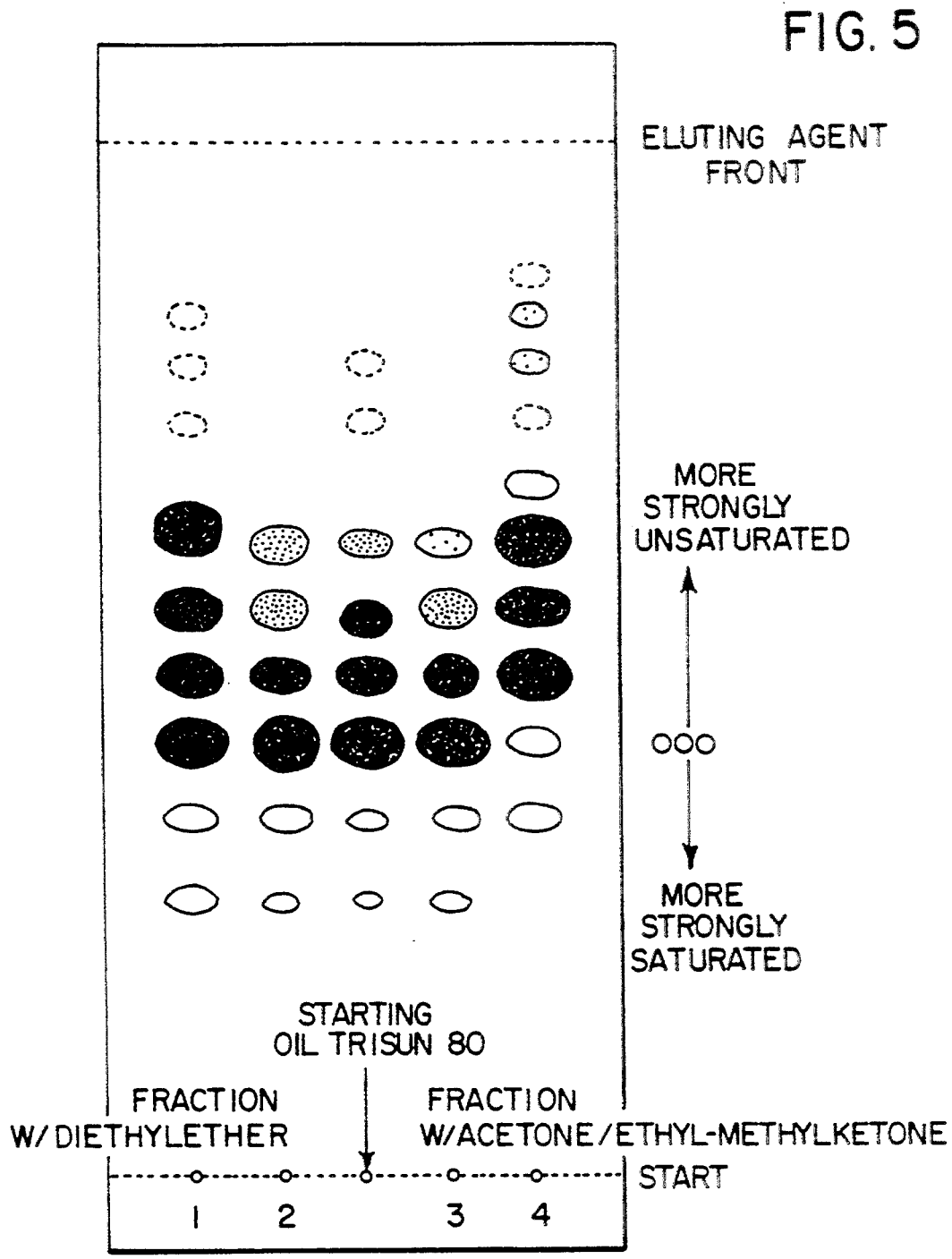
Figure 6:
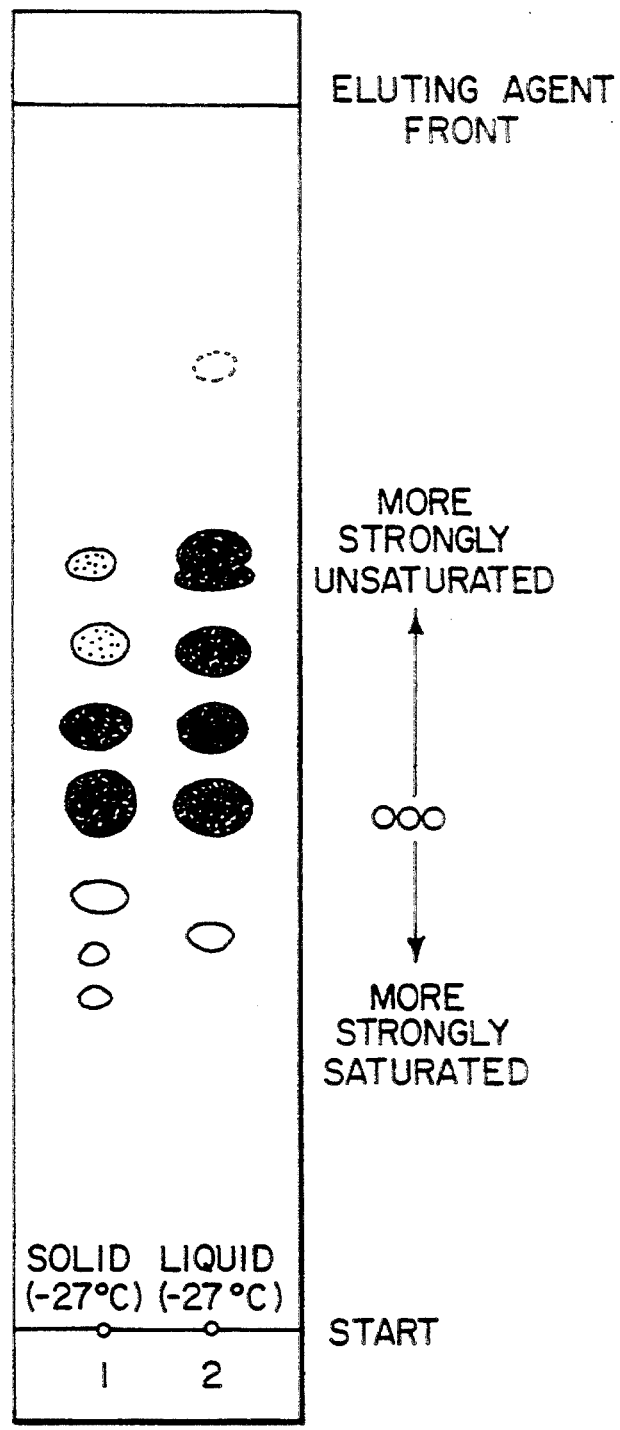

The chromatogram in FIG. 4 shows these phases compared with the starting oil. The plate shows that the solid phases which were separated out at −12° and −16° C. contain the triglycerides containing the saturated fatty acids to a reinforced degree. In the liquid phase separated out at the end at −27° C., the upper triglyceride spots above OOO can be seen from the chromatogram to be clearly reinforced.

The solid phase obtained at −27° C., enriched with trioleate shows a very strong trioleate chromatography spot as well as a weaker spot above (LOO) and 1 or 2 weaker spots below.

The following is a description of the materials and conditions employed in conjunction with FIG. 4:
Plate: HPTLC ready plate RP 18 without fluorescent indicator
  Merck: Type 5914
Eluting agent: acetone
Sample thinning: 20 mg/ml $CHCl_3$
Time of elution: 85 m.
Spraying reagent: molybdenum phosphoric acid (5% in ethanol)
The analyses show the following compositions for the solid and liquid phases:

| (1) Trisun in solid phase (−12° C.): | C16:0 = 12.96% |
|---|---|
| | C18:0 = 23.77% |
| | C18:1 = 42.55% |
| | C18:2 = 3.04% |
| | C20:0 = 2.89% |
| | C22:0 = 9.60% |
| | C24:0 = 3.80% |
| (2) Trisun in solid phase (−16° C.): | C16:0 = 4.10% |
| | C18:0 = 9.59% |
| | C18:1 = 60.94% |
| | C18:2 = 2.29% |
| | C22:0 = 23.09% |
| (3) Trisun in solid phase (−22° C.): | C16:0 = 4.04% |
| | C18:0 = 8.09% |
| | C18:1 = 82.10% |

-continued

|  |  |  |
|---|---|---|
|  | C18:2 = | 1.90% |
|  | C20:0 = | 0.70% |
|  | C22:0 = | 1.95% |
|  | C24:0 = | 0.77% |
| (4) Trisun in solid phase (−27° C.): | C16:0 = | 3.47% |
|  | C18:0 = | 4.44% |
|  | C18:1 = | 87.92% |
|  | C18:2 = | 2.31% |
|  | C20:0 = | 0.32% |
|  | C22:0 = | 0.65% |
|  | C24:0 = | 0.21% |
| Trisun in liquid phase (−27° C.): | C16:0 = | 4.58% |
|  | C18:0 = | 2.76% |
|  | C18:1 = | 63.16% |
|  | C18:2 = | 26.92% |
|  | C20:0 = | 0.21% |
|  | C22:0 = | 0.82% |
|  | C24:0 = | 0.30% |

With these fractionations the oleic acid content of 78.55% in the starting oil can be enriched to 87.92%.

EXAMPLE 3

Fractionation of Sunflower Oil with Acetone/Ethylmethylketone
Solvent employed:
Acetone: Ethylmethylketone=9:1 (by volume)
Fractionation 5 g Trisun 80 oil were mixed with 15 g of the solvent (1:3, parts by mass). At room temperature (20° C.) the oil dissolved in the solvent. The mixture was now kept for several hours in the deep freeze chest at −27° C. The resulting solid phase was separated through a pre-cooled fritted glass filter by suction with a water jet pump. At room temperature the solid phase liquified again. The solvent mixture was now removed from both phases in a rotary vaporizer.

| Yields: |  |
|---|---|
| Oil phase ( = solid phase): | 4.2 g |
| Oil in solvent phase (liquid phase): | 0.5 g |

Analysis:
The chromatogram (FIG. 5, samples 3 and 4) shows that the solvent phase 4 contained the triglycerides containing the multiple unsaturated fatty acid, markedly enriched. In comparison with the fractionating with diethylether (samples 1 and 2) mainly the triglycerides OOL, OOE, LOL are contained in the solvent phase 4, while in the diethylether solvent phase 1 OOO is also present. By means of the acetone/ethylmethylketone mixture a deliberate "severing" of the triglycerides containing the multiple unsaturated fatty acids is possible.
The oil phase 3 shows reduced intensity of the upper spots (apparently OOE+LOL) in comparison with the starting oil.
The following is a description of the materials and conditions employed in conjunction with FIG. 5:
Plate: HPTLC ready plate RP 18 without fluorescent indicator
Merck: Type No. 5914
Eluting agent: acetone
Sample thinning: 20 mg/ml CHCl$_3$
Time of elution: 1 h, 30 m.
Spraying reagent: molybdenum phosphoric acid (5% in ethanol)

EXAMPLE 4

Fractionation of Sunflower Oil with Diethylether
Solvent employed:
diethylether
Fractionation 10 g Trisun 80 oil were mixed with 10 diethylether (1:1, parts by mass). At room temperature (20° C.) the oil dissolved in the solvent. The mixture was now kept overnight (18 hours) in the deep freeze chest at −27° C. The coarsely granular, white solid phase was separated through a pre-cooled fritted glass filter by suction with a water jet pump. At room temperature the solid phase liquified again. The diethylether was now removed from both phases in a rotary vaporizer.

| Yields: |  |
|---|---|
| Oil phase ( = solid phase): | 7.0 g |
| Oil in solvent phase (liquid phase): | 2.9 g |

Analysis:
The chromatogram (FIG. 5, samples 1 and 2) shows that the solvent phase 1 contains the triglycerides containing the multiple unsaturated fatty acid, markedly enriched compared with the oil phase 2.

EXAMPLE 5

Fractionation of Sunflower Oil with Acetone/Diethylether
Solvent employed:
Acetone: Diethylether=9:1 (by volume)
Fractionation 5 g Trisun 80 oil were mixed with 15 g of the solvent (1:3, parts by mass). At room temperature a liquid phase was present. The mixture was now kept overnight in the deep freeze chest at −27° C. The resulting solid phase was separated through a pre-cooled fritted glass filter by suction with a water jet pump. At room temperature the solid phase liquified again. The solvent mixture was now removed from both phases in a rotary vaporizer.

| Yields: |  |
|---|---|
| Oil in the solid phase | 4.2 g |
| Oil in solvent phase | 0.5 g |

Analysis:
The chromatogram (FIG. 6) shows that the solvent phase contains the triglycerides containing the multiple unsaturated fatty acid, markedly enriched. The solid phase shows a reduction of these triglycerides compared with the starting oil. Fractionation with this solvent mixture proves to be readily possible. In comparison with the fractionation with and acetone/ethylmethylketone mixture however, more trioleate is contained in the solvent phase (cf. sample No. 4 in FIG. 5).
The following is a description of the materials and conditions employed in conjunction with FIG. 6:
Plate: HPTLC ready plate RP 18 without fluorescent indicator
Merck: Type No. 5914
Eluting agent: acetone
Sample thinning: 20 mg/ml CHCl$_3$
Time of elution: 1 h, 30 m.
Spraying reagent: molybdenum phosphoric acid (5% in ethanol)

In the following the advantages in derivative forming processes of the raw material obtained according to the invention will be set out:

(a) Single stage processes

As indicated, the raw material obtained with the invention is clearly superior in oleic acid to the raw material used to date in oleo-chemistry for derivative forming process. In ozonolysis increased yields of azelaic and pelargonic acids result. By-products and the expense of separating out these by-products, as necessary using the present raw material, are lost.

As well as ozonolysis, the transformation of oleic acid into hydroxystearic acid "hydroxylization", addition of water at the double bond) has special importance today and more so in the future. The hydroxystearic acids can be used in a variety of technical applications, such as in the production of lubricants in the manufacture of plastics for example. Starting therefrom, new kinds of fatty acid plastics can also be formed.

If the production of the hydroxystearic acid is effected from the conventional raw material (oleic acid-rich tallow fraction or tallow fatty acids fraction), a troublesome separation problem results in the separation of the di and trihydroxystearic acids necessarily also resulting from linoleic and linolenic acids.

Moreover, the multiple unsaturated fatty acids can lead to side reactions interfering with the hydroxylization reaction and to reaction compounds whose separation is extremely troublesome and annoying. Thus for example, radical reactions, conversion reactions, auto-oxidization reactions and many others can take place.

A further known derivative forming reaction with oleic acid is the transformation of the oleic acid into the dihydroxystearic acid by oxidization, where for example permanganate, dichromate, osmium tetroxide or $H_2O_2$ are used as oxidizing agents. The reaction can be carried out with the triglycerides themselves or the corresponding fatty acids and fatty acid derivatives. All these oxidizing agents can also initiate reactions with the linoleic and linolenic acids present as impurities in the conventional raw material, so that tetra and hexahydroxystearic acid can result as well as the dihydroxystearic acid. These present the isolation of the desired dehydroxystearic acid or its derivatives.

Moreover side reactions can be caused which are typical of multiple unsaturated fatty acids and reaction compounds result which additionally seriously interfere with isolation of the 9, 10- dehydroxystearic acid, as results in the oxidization of oleic acid. Reference has already been made to the increased use of oxidizing agents.

Account must also be taken of the fact that the conversion with multiple unsaturated fatty acids can take place at the respective double bonds at varying speeds and non-uniformly—not as in the case of oleic acid as sole unsaturated fatty acid. The spectrum of the possible annoying by-products hampering the isolation of the desired oleic acid derivatives is thus decidedly increased.

In the case of use of the raw material according to the invention all these difficulties disappear.

A further, industrially interesting derivative forming reaction is the epoxidization of fatty acid double bonds to the corresponding epoxy fatty acids. The most important industrial products here are the epoxidized oils of such vegetable oils as contain a high proportion of unsaturated fatty acids. The epoxy oils are used as stabilizers above all in the plastics manufacturing industry.

Epoxidized oils can also be used as the basic material for the production of chemical reaction products. This applies especially when it is possible to isolate homogenous chemical compounds therefrom. If conventional raw materials, themselves with heavy oleic acid contents, as are obtained from tallow, are subjected to epoxidization, by-products also result, which hamper the further use of the epoxy triglycerides, especially for chemically homogenous raw chemical materials.

If one starts from untreated high oleic oils, an epoxy oil results with a markedly higher epoxy oleic acid proportion than with enriched tallow as the starting material; because of the presence of linoleic and linolenic acids in the raw material it is however of extremely heterogenous composition. Similarly to the oxidation of the double bonds to dioles, a solid product at room temperature results from the epoxidization, which has however a waxy and non-crystalline, runny characteristic. In contrast, if a start is made from oleic acid raw material according to the invention, a product is obtained which exhibits a clearly crystalline character. Using this product, chemical reaction products can be manufactured substantially more easily, since such side reactions and reaction products are rules out which can be formed from the products of epoxidization of linoleic and linolenic acid. (Reference should be made to the fact that both linoleic and linolenic acid—other than is the case with oleic acid—contain one and two active methyl groups respectively and are thus prone to reactions which cannot be carried out starting with oleic acid.)

(b) Multistage processes:

If a halogen hydride is taken up by the oleic acid with the object of obtaining corresponding amino acids in this manner by conversion with ammonia, 9- or 10- aminostearic acid is obtained as the reaction product starting from the raw material produced in accordance with the invention, through the corresponding keto-compounds. No other constituents of the raw material react. If however linoleic and linolenic acid are present, the spectrum of possible side reactions is so impossible to comprehend that separation of chemically homogenous amino acids appears hardly possible. It is thus understandable that this type of conversion comprising a plurality of steps has to date achieved hardly any industrial importance. The same applies to a variety of other reactions. For example, reference may be made to the analogous reactions for generating aminocapronic acid, the starting material for nylon.

Oleic acid can be transformed oxidatively into 9- or 10- ketostearic acid. Transformed by the Schmidt or Beckmann reaction, there results a splitting of the carbon chain of the fatty acid with formation of the following compounds: 1-aminononane, 1-aminodecane, pelargonic acid, decanoic acid, both linearly formed and un-branched, dicarboxylic acid with chain lengths of $C_{10}$ and $C_9$ and linear amino acids with terminal amino groups and chain lengths of $C_{10}$ and $C_9$. All resulting compounds can suit high-value applications. The separation of the resulting compound types—amines, amino acids; monocarboxylic acids, dicarboxylic acids—is state of the art.

If a start is made from raw materials available at present from tallow or from similar substances rich in oleic acid but containing many unsaturated fatty acids as by-products, such as high oleic oils for example, there results a substantially wider spectrum, for which isolation of the resulting reaction products is hardly possible.

The oleic acid fraction obtained according to the invention thus represents for the first time a raw material from which homogenous chemical reactions on the double bond of the oleic acid can be carried out, even though it itself is not of homogenous chemical composition. Accordingly the oleic acid is available as a chemical base material in the first place in a simple and economical manner.

We claim:

1. A process for producing a triglyceride oil component essentially free from other components hampering further processing comprising:
   (a) selecting a component of a vegetable oil having a single reactive fatty acid portion which predominates in the fatty acid pattern with a content of at least about 80%; and
   (b) cooling the component of step a in a cooling step while adjusting the temperature to form predominantly solid and liquid phases so that the particularly hard to solidify or readily soluble triglycerides in the starting material remain at least substantially liquid or in solution in the liquid phase.

2. The process according to claim 1, wherein there is produced a triglyceride of single fatty acids.

3. The process according to claim 1, wherein the vegetable oil is a derivative containing an unaltered carbon framework.

4. The process according to claim 1, wherein the cooling and separation phases are repeated.

5. The process according to claim 1, wherein the solid phase is dissolved and cooled in a second cooling step at a temperature different from a temperature of the cooling step.

6. A process according to claim 1, wherein the hard to solidify or readily soluble triglycerides in the liquid phase are separated and subsequently employed for further processing.

7. A process according to claim 6, wherein the liquid phase is subjected to a second cooling step.

8. A process according to claim 5, wherein the cooling temperature of the cooling step is lower than that of the second cooling step.

9. A process according to claim 7, wherein the cooling temperature of the cooling step is lower than that of the second cooling step.

10. A process according to claim 1, wherein there are used as a starting material natural oils with fatty acid contents of at least about 80% oleic acid in the fatty acid pattern and are high oleic oils.

11. A process according to claim 2, wherein there are used as a starting material natural oils with fatty acid contents of at least about 80% oleic acid in the fatty acid pattern and are high oleic oils.

12. A process according to claim 1, wherein there are used as a starting material one of the following oils: high oleic oil of sunflowers, euphorbia lathyris, epoxidized high oleic oil, hydrolyzed epoxy high oleic oil, or keto high oleic oil, castor oil, and hydrogenated castor oil.

13. A process according to claim 6, wherein there are used as a starting material one of the following oils: high oleic oil of sunflowers, euphorbia lathyris, epoxidized high oleic oil, hydrolyzed epoxy high oleic oil, keto high oleic oil, castor oil, and hydrogenated castor oil.

14. A process according to claim 5, wherein the cooling temperature of the cooling step is adjusted to about $-27°$ C. to $-30°$ C. and that of the second cooling step to about $-4°$ to $-6°$ C.

15. A process according to claim 9, wherein the cooling temperature of the cooling step is adjusted to about $-27°$ to $30°$ C. and that of the second cooling step to about $4°$ to $-6°$ C.

16. A process according to claim 1, wherein the vegetable oil is used in a solution in acetone or acetic acid ethyl ester.

17. A process according to claim 2, wherein the vegetable oil is used in a solution in acetone or acetic acid ethyl ester.

18. A process according to claim 3, wherein the vegetable oil is used in a solution in acetone or acetic acid ethyl ester.

19. A process according to claim 4, wherein the vegetable oil is used in a solution in acetone or acetic acid ethyl ester.

20. A process according to claim 5, wherein the vegetable oil is used in a solution in acetone or acetic acid ethyl ester.

21. The process according to claim 1, wherein the triglyceride oil component is a mixture.

22. A process for producing a triglyceride oil mixture essentially free from components hampering further processing comprising:
   (a) selecting a vegetable oil containing at least about 75% linoleic acid in the reactive fatty acid portion; and
   (b) cooling the oil in a cooling step while adjusting the temperature to form predominantly solid and liquid phases so that the particularly hard to solidify or readily soluble triglycerides in the starting material remain at least substantially liquid or in solution in the liquid phase.

* * * * *